United States Patent [19]

Chastain et al.

[11] Patent Number: 5,308,871
[45] Date of Patent: May 3, 1994

[54] METHOD OF KILLING YEAST OR FUNGI WITH DIHYDROCARVONE

[75] Inventors: Doyle E. Chastain, 137 Birch St., Titusville, Fla. 32780; W. Eugene Sanders, Jr.; Christine C. Sanders, both of Omaha, Nebr.

[73] Assignee: Doyle E. Chastain, Titusville, Fla.

[21] Appl. No.: 993,026

[22] Filed: Dec. 18, 1992

[51] Int. Cl.$^5$ .................. A01N 35/00; A61K 31/12
[52] U.S. Cl. .................................................. 514/690
[58] Field of Search .................................... 514/690

[56]  References Cited

U.S. PATENT DOCUMENTS

| Re. 28,263 | 12/1974 | Gauvreau | 514/358 |
|---|---|---|---|
| 2,803,647 | 8/1957 | Bain et al. | 260/489 |
| 2,863,882 | 12/1958 | Bain et al. | 260/348.5 |
| 3,014,047 | 12/1961 | Bain et al. | 260/348 |
| 3,743,747 | 7/1973 | Whitehurst | 424/333 |
| 5,153,229 | 10/1992 | Chastain et al. | 514/763 |

OTHER PUBLICATIONS

Jour. Amer. Pharm. Assn., Maruzzella et al. vol. 47, No. 4, pp. 250–254 (Apr. 1958).
Plant Disease Reporter, Maruzzella et al. vol. 43, No. 11, pp. 1143–1147 (1959).
Food Technology, Murdock et al. vol. 14, No. 9, pp. 441–445 (1960).
Plant Disease Reporter, Maruzzella et al. vol. 44, No. 10, pp. 789–792 (1960).
Botanical Gazette, French pp. 194–198 (Mar. 1961).
Chemical Abstracts, Blumann et al. vol. 63, p. 1819 (1965).
Nature, Zuckerman vol. 168, p. 517 (Sep. 1951).
Agric. Biol. Chem., Kurita et al. vol. 45, No. 4, pp. 945–952 (1981).
Herba Hungarica, Hethelyi et al. vol. 27, No. 2–3, pp. 89–105 (1988).

Primary Examiner—Allen J. Robinson
Attorney, Agent, or Firm—Arthur G. Yeager; Earl L. Tyner

[57]  ABSTRACT

A method of killing yeast or fungi which comprises treating the yeast or fungi with a toxic amount of dihydrocarvone.

3 Claims, No Drawings

METHOD OF KILLING YEAST OR FUNGI WITH DIHYDROCARVONE

TECHNICAL FIELD

The object of this invention is to demonstrate a method of using dihydrocarvone to kill yeast and fungi.

BACKGROUND OF THE INVENTION (1) Field of the Invention

During the study of limonene as a hand cleaner, the applicants found that fully oxygenated limonene is a fungicide. A reveiw of the literature revealed that oxygenated limonene contains several oxidation products including: limonene-1,2-oxide, limonene-8,9-oxide, 1-menthene-9-al, α-2,8-p-menthadiene-1-ol, β-2,8p-menthadiene-1-ol, dihydrocarvone, β-cymenol, carvone, cis-carveol, and trans-carveol, as :;as outlined by Bain in U.S. Pat. Nos 2,863,882 and 3,014,047. Blumann listed the compounds formed by the auto-oxidation of limonene in *Chemical Abstracts*, Volume 63, 1965, on page 1819, which included cis-carveol, trans-carveol, trans-p-menth-8-ene-1,2-diol, limonene 1,2-epoxide, limonene 8,9-epoxide, cis and trans-p-mentha-2,8-dien-1-01, and perillyl alcohol. Even though it was unexpected, the applicants found that effecitve concentrations of dihydrocarvone kills yeast and fungicidal concentrations of dihydrocarvone kills fungi.

Dihydrocarvone is a monocyclic monoterpene with the following chemical formula:

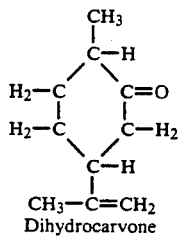

Dihydrocarvone

Dihydrocarvone is an oil with a terpenic aroma. It is insoluble in water and glycerine. Dihydrocarvone is soluble in alcohol and is miscible in corn oil, olive oil, and soybean oil, etc. Dihydrocarvone has been used as a bactericide, but heretofore, it has never been demonstrated to kill yeast or fungi.

Bain in U.S. Pat. No. 2,803,647 showed his method of producing carveol and dihydrocarvone and their esters.

(2) Description of the Prior Art

Zukerman studied the effect of auto-oxidized limonene on bacteria. He found it was weakly bacteriostatic, was unstable, and that it lost its bacteriostatic effect on keeping as was discussed in *Nature* 168: 517 (1951). He never studied oxidized limonene nor dihydrocarvone for fungicidal activity. Kurita investigated the fungicidal activity of several components of essential oils in *Biol. Chem.*, 45(4), 945–952, 1981, and noted that cineole, anethole, safrole, d-limonene, α-pinene, β-pinene, camphene, β-myrcene, caryophyllene, β-cymene, d-camphor, benzaldehyde, vanillin, and furfural are not fungicidal while cinnamaldehyde, phenol, perillyl aldehyde, citral, perillyl alcohol, geraniol, citronellol, 1-nonanol, 1-decanol 1-menthol and borneol have minimal to good fungicidal activity. He never studied the anti-yeast or anti-fungal activity of dihydrocarvone.

Peter Tetenyi et al studied essential oils obtained from twelve different specimens of *Tanacetum vulgare* L. and found eight of the twelve specimens to be bactericidal in a concentration of 100 ug/ml against 85–90% of nineteen different bacteria and 100% fungicidal against sixteen species of fungi in a concentration of 50 ug/ml. He delineated numerous chemical components in the oils but he never studied dihydrocarvone or any of the individual components in the oils for anti-bacterial, anti-yeast and/or anti-fungal activity as was outlined in *Herba Hungarica*, 1981, Tom 20, No. 1-2, pages 57–74. In Botanical Gazette 122, 194–8 (1961), R. C. French showed that carveol and dihydrocarveol stimulate the germination of wheat stem rust uredospores suggesting that carveol and dihydrocarveol promote the growth of fungi. J. C. Maruzzella and L. Liguori reported the in vitro anti-fungal activity of essential oils in the *Journal of the American Pharmaceutical Association*, Vol. XLVII, No. 4, April 1958, pages 250–4, but they did not study the fungicidal activity of dihydrocarvone. J. C. Maruzzella and Jerry Balter showed the action of essential oils on phytopathogenic fungi in the *Plant Disease Reporter* Vol. 43, No. 11, Nov. 1959, pages 1143–1147, but they did not study the anti-yeast or the anti-fungal activity of dihydrocarvone. Gauvreau showed a means of producing disinfecting compositions in U.S. Pat. No. 3,595,975 by combining cetyl pyridinium with terpenes to form antiseptics. Gauvreau never studied the use of dihydrocarvone alone nor in combination with cetyl pyridinium. Chastain and Sanders discovered a method of making limonene bactericidal and fungicidal as described in U.S. Pat. No. 5,153,229, but they never studied dihydrocarvone for bactericidal nor fungicidal activity. A. Morel revealed the sterilizing action of carveol, dihydrocarveol, and their ozonization products in *Comp. Rend. Soc. Biol.* Volume 115, pages 536–8 (1934). He demonstrated the bactericidal activity of carveol and dihydrocarveol but he never studied their anti-yeast or anti-fungal activity. D. D. Whitehead in U.S. Pat. No. 3,743,747 showed the fungicidal activity of several oxo-derivatives of limonene and dipentene, but he never studied the anti-yeast or anti-fungal activity of dihydrocarvone. J. C. Maruzzella et al reported the action of odoriferous organic chemicals and essential oils on wood-destroying fungi in the *Plant Disease Reporter* Vol 44, No. 10 (1960); dihydrocarvone was never studied. Murdock and Allen showed the germicidal effect of sodium benzoate against yeast is enhanced by orange peel oil and d-limonene (stripper oil), as was reported in *Food Technology*, Vol 14, No. 9, 1960, pages 441–5. They never studied the action of dihydrocarvone against yeast or fungi. Kellner et al studied ethereal oils for antimicrobial activity, but they never studied the oils nor any of their chemical constituents for anti-yeast or anti-fungal activity as was outlined in *Arzneimittel-Forschung* 5 224–9 (1955).

It should be pointed out that the drugs which are bactericidal are usually not fungicidal, and drugs which are fungicidal are usually not bactericidal. In humans, the use of bactericidal antibiotics frequently promotes the growth of yeast. Table A, which follows, exemplifies the anti-bacterial, anti-yeast and anti-fungal activity of several commonly used anti-bacterial, anti-yeast, and anti-fungal antibiotics.

TABLE A

| ANTIBIOTICS | ANTIBIOTIC ACTIVITY AGAINST | | | | |
|---|---|---|---|---|---|
| | Gm + Bact | Gm − Bact | A F Bact | Yeast | Fungi |
| A. ANTIBACTERIAL | | | | | |
| 1. Ampicillin | YES | YES | NO | NO | NO |
| 2. Cephalothin | YES | YES | NO | NO | NO |
| 3. Chloramphenicol | YES | YES | NO | NO | NO |
| 4. Erythromycin | YES | NO | NO | NO | NO |
| 5. Ethambutol | NO | NO | YES | NO | NO |
| 6. Gentamicin | YES | YES | NO | NO | NO |
| 7. Isoniazid | NO | NO | YES | NO | NO |
| 8. Nitrofurantoin | NO | YES | NO | NO | NO |
| 9. Penicillin | YES | NO | NO | NO | NO |
| 10. Rifampin | YES | NO | YES | NO | NO |
| 11. Streptomycin | YES | YES | YES | NO | NO |
| 12. Sulfonamides | NO | YES | NO | NO | NO |
| 13. Tetracycline | YES | YES | NO | NO | NO |
| 14. Vancomycin | YES | YES | NO | NO | NO |
| B. ANTIYEAST | | | | | |
| 1. Nystatin | NO | NO | NO | YES | NO |
| 2. Gentian Violet | NO | NO | NO | YES | NO |
| C. ANTIFUNGAL | | | | | |
| 1. Chlotrimazole | NO | NO | NO | YES | YES |
| 2. Griseofulvin | NO | NO | NO | NO | YES |

Gm + Bact = Gram Positive Bacteria, Gm − Bact = Gram Negative Bacteria, A F Bact = Acid Fast Bacteria, YES = Kills Organism, NO = No Activity Against Organism It should be noted in the table above that none of the anti-bacterial antibiotics kill yeast nor fungi, and none of the anti-yeast nor anti-fungal antibiotics kill bacteria. Thus an anti-fungal or anti-yeast antibiotic is not expected to kill bacteria, and an anti-bacterial antibiotic is not expected to kill yeast or fungi. Anti-fungal antibiotics do not necessarily kill yeast, and anti-yeast antibiotics do not necessarily kill fungi.

Several differences between yeast and fungi are known and are listed. For instance: (1) yeast can be grown in a culture in 24–48 hours while a fungus requires 7–14 days to grow in a culture. (2) Yeast grow on blood agar while fungi grow on sabouraud dextrose agar. (3) The use of anti-bacterial antibiotics in humans promotes the grow of yeast but the use of anti-bacterial antibiotics in humans does not promote the growth of fungi. (4) Several anti-yeast antibiotics do not kill fungi and several anti-fungal antibiotics do not kill yeast.

DISCLOSURE OF THE INVENTION

This invention relates to the use of dihydrocarvone to kill yeast and fungi. Dihydrocarvone is an oil which is available commercially, but heretofore, it has not been shown to kill yeast or fungi. It is slightly viscous, and when applied, readily adheres to glass, metal, wood, cloth, rope, book covers, paper, cement, ceramics, paint, plastic, plant surfaces, skin, mucus membranes, and teeth leaving an oily film. Because it is not soluble in water its adherence to surfaces allows prolonged exposure and makes dihydrocarvone ideal for treating yeast and fungus infections of plants, animals, and humans.

The exact method of killing yeast and fungi is unknown, but it is thought that dihydrocarvone kills yeast and fungi by lysing the cell membrane of the organism which is lethal to the organism.

In practice, any surface, on which it is desirable to kill or prevent the growth of yeast or fungi, is treated with effective concentrations of dihydrocarvone to kill yeast, or fungicidal concentrations of dihydrocarvone to kill fungi by swabbing, wiping, painting, washing, brushing, spraying, or any other direct application technique. Alternatively, dihydrocarvone can be incorporated in creams, ointments, tinctures, gels, suppositories, paints, sprays, aerosols, toothpastes, solutions, emulsions, soaps, scrubs, mouthwashes, or antiseptics and applied anywhere it is desirable to kill or prevent the growth of yeast or fungi.

BEST MODE FOR CARRYING OUT THE INVENTION

The following examples are illustrative of the best mode for carrying out the invention. They are, obviously, not to be construed as limitative of the invention since various other embodiments can readily be evolved in view of the teachings provided herein.

EXAMPLE 1

Anti-Yeast And Anti-Fungal Activity of Dihydrocarvone

The anti-yeast and anti-fungal compound contemplated by this invention is dihydrocarvone which was studied for anti-yeast and anti-fungal activity. The organisms tested included the yeast, *Candida albicans*, that causes infections of skin and mucus membranes; the cutaneous fungus, *Microsporum canis*, that infects man and animals, and the mildew causing fungi *Aureobasidium pullulans* OM 279C, *Cladosporium cladosporiodes* OM 489, and *Phialophora lignicola* OM 5922. The minimal effective concentration of dihydrocarvone needed to kill yeast and the fungicidal concentration needed to kill fungi are listed in Table B below. The dihydrocarvone used in the tests were obtained from Aldrich Chemical Company, Milwaukee, Wis. The Catalogue Number and Lot Number for the dihydrocarvone were 21,842-1 and TD092197 respectively.

TABLE B

ANTI-YEAST AND ANTI-FUNGAL ACTIVITY OF dl DIHYDROCARVONE

| ORGANISM | MINIMUM EFFECTIVE CONCENTRATION | | |
|---|---|---|---|
| A. YEAST | 10 MIN | 60 MIN | 24 HOURS |
| 1. *Candida albicans* | >0.016 | 0.016 | 0.005 |
| B. FUNGI | MINIMUM FUNGICIDAL CONCENTRATION | | |
| 1. *Microsporum canis* | >0.16 | >0.16 | 0.0012 |
| 2. *Aureobasidium pullulans* Om 279C | >0.16 | 0.06 | 0.0012 |

TABLE B-continued

ANTI-YEAST AND ANTI-FUNGAL ACTIVITY OF dl DIHYDROCARVONE

| | | | |
|---|---|---|---|
| 6. *Cladoscorium cladosporiodes* OM 489 | >0.16 | 0.16 | 0.0012 |
| 7. *Phialophora lignicola* | 0.16 | 0.10 | 0.0012 |

OM 5922

The standard assay used to test the activity of dihydrocarvone against yeast and fungi was as follows: various dilutions of dihydrocarvone were individually prepared in Sabouraud dextrose broth medium. An inoculum of $10^6$ colony-forming units (CFU/ml) of yeast or fungi were introduced into each test, after which it was incubated at 37° C. in air, and subcultured (0.01 ml) at 10 minutes, 60 minutes, and 24 hours onto agar media free of dihydrocarvone. Results were expressed as the minimal lethal concentration, i.e. the lowest concentration of dihydrocarvone (ml dihydrocarvone/total ml of test) with no detectable viable colonies following subculture onto media free of dihydrocarvone.

Details of each assay are presented in Table C which follows.

TABLE C

Test conditions used to assay the anti-yeast and anti-fungal activity of dihydrocarvone

| ORGANISM | BROTH MEDIUM | SUBCULTURE AGAR MEDIUM | INCUBATION CONDITIONS |
|---|---|---|---|
| 1. Yeast | Sabouraud Dextrose | 5% sheep blood | air at 37° C. |
| 2. Fungi | Sabouraud Dextrose | Sabouraud Dextrose agar | air at 30° C. |

EXAMPLE 2

Formulations Which Include The Anti-Yeast And The Anti-Fungal Compound Dihydrocarvone The following formulations are prepared using dihydrocarvone in liquids, gels, soaps, paints, pastes, creams, ointments, solutions, tinctures, suppositories, tampons, aerosols, and emulsions. When yeast or fungi are treated with dihydrocarvone containing formulations, the formulations kill or prevent the growth yeast or fungi.

| CHEMICAL | % OF TOTAL | RANGE | ACTION |
|---|---|---|---|
| A. LIQUIDS | | | |
| 1. SOLUTIONS OR SPRAYS | | | |
| a. Dihydrocarvone | 5.0% | 0.1–50% | fungicide |
| Corn Oil | 95.0% | 50–99.9% | diluent |
| | 100.0% | | |
| b. Dihydrocarvone | 1.0% | 0.1–50% | fungicide |
| Ethyl Alcohol | 99.0% | 50–99.9% | diluent |
| | 100.0% | | |
| 2. MOUTHWASH | | | |
| a. Dihydrocarvone | 50.0% | 0.1–50% | anti-yeast |
| Flavor | 2.0% | 1–5% | flavor |
| Ethyl Alcohol | 48.0% | 45–98.9% | diluent |
| | 100.0% | | |
| B. DENTIFRICE | | | |
| 1. LIQUID | | | |
| Liquid soap concentrate | 5.0% | 2–10% | surfactant |
| Saccharin | 0.2% | 0.1–1.0% | flavor |
| Clove Oil | 1.0% | 0.5–3.0% | flavor |
| Cinnamon Oil | 0.5% | 0.5–3.0% | flavor |
| Peppermint Oil | 0.5% | 0.5–3.0% | flavor |
| Ethyl Alcohol | 42.6% | 29.5–95.3% | diluent |
| Color | 0.2% | 0.1–0.5% | color |
| Dihydrocarvone | 50.0% | 1–50% | fungicide |
| | 100.0% | | |
| Sodium monofluorophosphate | 0.8% | 0.5–1.5% | antiplaque |
| Dihydrocarvone | 50.0% | 1–50% | anti-yeast |
| Hydrated silica xerogel | 10.0% | 8–15% | abrasive |
| Hydrated thickening silica | 8.5% | 5–10% | binder |
| Sorbitol 70% solution | 18.8% | 5–73.3% | humectant |
| Polyethylene glycol 32 | 5.0% | 3–7% | bodying agent |
| Sodium lauryl sulfate | 1.5% | 1–2% | surfactant |
| Carboxymethyl cellulose gum | 1.0% | 0.5–2% | binder |
| S D alcohol | 1.0% | 0.5–2% | stabilizer |
| Flavor | 3.0% | 2–4% | flavor |
| Saccharin | 0.2% | 0.1–0.5% | flavor |
| F D & C Green #3 | 0.1% | 0.1–0.5% | color |
| F D & C Yellow #10 | 0.1% | 0.1–0.5% | color |
| | 100.0% | | |
| 3. PASTE | | | |
| Sodium monofluorophosphate | 0.8% | 0.5–1.5% | antiplaque |
| Dihydrocarvone | 50.0% | 1–50% | fungicide |
| Dicalcium phosphate | 22.0% | 20.4–30% | abrasive |

-continued

| CHEMICAL | % OF TOTAL | RANGE | ACTION |
|---|---|---|---|
| dihydrate | | | |
| Water | 16.0% | 11.1–69.5% | diluent |
| Glycerine | 5.1% | 4.5–12.5% | bodying agent |
| Flavor | 2.0% | 2–3% | flavor |
| Sodium lauryl sulfate | 1.5% | 1–2% | surfactant |
| Carboxymethyl cellulose gum | 1.4% | 0.5–2.0% | binder |
| Tetrasodium pyrophosphate | 1.0% | 0.5–2.0% | binder |
| Sodium saccharin | 0.2% | 0.1–0.5% | flavor |
| | 100.0% | | |

C. OINTMENTS & SUPPOSITORIES WITH AND WITHOUT HYDROCORTISONE

1. OINTMENT WITH HYDROCORTISONE

| CHEMICAL | % OF TOTAL | RANGE | ACTION |
|---|---|---|---|
| Dihydrocarvone | 1.0% | 0.1–15.0% | fungicide |
| Polyethylene glycol 3350 | 59.5% | 48.5–59.7% | bodying agent & emulsifier |
| Polyethylene glycol 400 | 39.5% | 31.5–39.7% | bodying agent & emulsifier |
| Hydrocortisone | 1.0% | 0.5–5.0% | anti-inflammatory |
| | 100.0% | | |

2. OINTMENT WITHOUT HYDROCORTISONE

| CHEMICAL | % OF TOTAL | RANGE | ACTION |
|---|---|---|---|
| Dihydrocarvone | 1.0% | 0.1–15 0% | fungicide |
| Polyethylene glycol 3350 | 59.5% | 51.0–59.95% | bodying agent & emulsifier |
| Polyethylene glycol 400 | 39.5% | 34.0–39.95% | bodying agent & emulsifier |
| | 100.0% | | |

3. SUPPOSITORY WITHOUT HYDROCORTISONE

| CHEMICAL | % OF TOTAL | RANGE | ACTION |
|---|---|---|---|
| Dihydrocarvone | 1.0% | 0.1–15% | fungicide |
| Polyethylene glycol 1000 | 9.5% | 51.0–59.95% | bodying agent & emulsifier |
| Polyethylene glycol 3350 | 39.5% | 34.0–39.95% | bodying agent & emulsifier |
| | 100.0% | | |

4. SUPPOSITORY WITH HYDROCORTISONE

| CHEMICAL | % OF TOTAL | RANGE | ACTION |
|---|---|---|---|
| Dihydrocarvone | 1.0% | 0.1–15% | anti-yeast |
| Polyethylene glycol 1000 | 74.0% | 60.0–75.2% | bodying agent & emulsifier |
| Polyethylene glycol 3350 | 24.0% | 20.0–24.2% | bodying agent & emulsifier |
| Hydrocortisone | 1.0% | 0.5–5.0% | anti-inflammatory |
| | 100.0% | | |

D. CREAM WITHOUT HYDROCORTISONE

| CHEMICAL | % OF TOTAL | RANGE | ACTION |
|---|---|---|---|
| 1. Dihydrocarvone | 1.0% | 0.1–15.0% | fungicide |
| Cetyl alcohol | 15.0% | 12.0–18.0% | thickener |
| Arlacel 165** | 5.0% | 3.5–7.5% | emulsifier |
| Sorbitol 70% solution | 5.0% | 3.5–8.0% | humectant |
| Water | 74.5% | 51.5–80.9% | diluent |
| | 100.0% | | |
| 2. Dihydrocarvone | 1.0% | 0.1–15.0% | fungicide |
| Spermaceti wax | 12.5% | 10.0–15.0% | thickener |
| Sorbitan monostearate Polyethylene 20 | 10.0% | 7.5–12.5% | emulsifier |
| Sorbitan monostearate | 6.0% | 4.0–8.0% | emulsifier |
| Water | 75.5% | 49.5–78.4% | diluent |
| | 100.0% | | |

E. CREAMS WITH HYDROCORTISONE

| CHEMICAL | % OF TOTAL | RANGE | ACTION |
|---|---|---|---|
| 1. Dihydrocarvone | 1.0% | 0.1–15.0% | fungicide |
| Cetyl alcohol | 15.0% | 12.0–18.0% | thickener |
| Arlaoel 165** | 5.0% | 3.5–7.5% | emulsifier |
| Sorbitol 70% solution | 5.0% | 3.5–8.0% | humectant |
| Hydrocortisone | 1.0% | 0.5–5.0% | anti-inflammatory |

-continued

| CHEMICAL | % OF TOTAL | RANGE | ACTION |
|---|---|---|---|
| Water | 73.0% | 46.5–80.4% | diluent |
| | 100.0% | | |

*Croda, Inc., 51 Madison Ave., New York, New York 10010
**Glycerol monostearate and polyoxyethylene stearate ICI of America (Formerly Atlas Chemical Industries), Wilmington, Delaware 19899

F. TAMPONS

| | | | |
|---|---|---|---|
| 1. Dihydrocarvone 2 cc 2 Gm | 8% | 1–15% | fungicide |
| Tampon 23 Gm | 92% | 85–99% | reservoir |
| | 100.0% | | for fungicid |

G. AEROSOLS WITHOUT HYDROCORTISONE

| | | | |
|---|---|---|---|
| 1. Dihydrocarvone | 5.0% | 0.5–50% | fungicide |
| Ethyl alcohol | 95.0% | 50–99.5% | diluent |
| | 100.0% | | |

Pressurized nitrogen propellant at 100–125 psig

| | | | |
|---|---|---|---|
| 2. Dihydrocarvone | 10.0% | 0.5–50.0% | fungicide |
| Soybean oil | 90.0% | 50.0–99.5% | diluent |
| | 100.0% | | |

Pressurized nitrogen propellant at 100–125 psig

H. AEROSOL WITH HYDROCORTISONE

| | | | |
|---|---|---|---|
| 1. Dihydrocarvone | 1.0% | 0.5–50% | fungicide |
| Soybean oil | 98.0% | 45–99.0% | diluent |
| Hydrocortisone | 1.0% | 0.5–5.0% | anti- |
| | 100.0% | | inflammatory |

Pressurized nitrogen propellant at 100–125 psig

I. OIL IN WATER EMULSION

| | | | |
|---|---|---|---|
| 1. Dihydrocarvone | 0.1% | 0.1–50% | fungicide |
| Corn oil | 10.0% | 10–15% | oil |
| Arlacel 40** | 2.0% | 1–3% | emulsifier |
| Tween 40 | 3.0% | 2–4% | emulsifier |
| 2. Water | 84.9% | 28–86.9% | diluent |
| | 100.0% | | |

Heat 1 to 70° C. Heat 2 to 72° C. Add 2 to 1 with agitation. Stir until cooled to room temperature.

J. OIL IN WATER EMULSION WITH SOAP (FUNGICIDAL SOAP)

| | | | |
|---|---|---|---|
| 1. Dihydrocarvone | 1.0% | 0.1–25% | fungicide |
| Corn oil | 30.0% | 20.0–40.0% | oil |
| Arlacel 40** | 2.0% | 1.0–3.0% | emulsifier |
| Tween 40 | 3.0% | 2.0–4.0% | emulsifier |
| Liquid soap concentrate | 3.5% | 2.5–5.0% | surfactant |
| 2. Water | 60.5% | 23–74.4% | diluent |
| | 100.0% | | |

Heat 1 to 70° C. Heat 2 to 72° C. Add 2 to 1. Stir until cooled to room temperature.

K. WATER IN OIL EMULSION

| | | | |
|---|---|---|---|
| 1. Dihydrocarvone | 1.0% | 0.1–25% | fungicide |
| Arlacel 186** | 3.0% | 2.0–4.0% | emulsifier |
| Soybean oil | 15.0% | 10.0–25.0% | oil |
| Ceresin wax | 0.5% | 0.3–0.6% | thickener |
| Beeswax | 0.5% | 0.3–0.6% | thickener |
| Tween 80 | 0.5% | 0.3–0.6% | emulsifier |
| 2. Water | 79.5% | 44.2–87.0% | diluent |
| | 100.0% | | |

Heat 1 to 70° C. Heat 2 to 72° C. Add 2 to 1 with continuous agitation.

L. PAINT

1. ENAMEL

| | | | |
|---|---|---|---|
| Dihydrocarvone | 1.0% | 1–10% | fungicide |
| Titanium dioxide | 14.91% | 12–16% | pigment |
| Calcium carbonate | 29.83% | 25–35% | pigment |
| Silicate | 4.81% | 3–6% | pigment |
| Soya alkyd resin | 25.72% | 22–28% | pigment (binder) |
| Mineral spirits | 23.73% | 5–37% | solvent |
| | 100.00% | | (thinner) |

2. LATEX

| | | | |
|---|---|---|---|
| Dihydrocarvone | 1.0% | 1–10% | fungicide |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.47% | 6–10% | solvent |

| CHEMICAL | % OF TOTAL | RANGE | ACTION |
|---|---|---|---|
| | -continued | | |
| Water | 34.0% | 12-50% | (thinner) solvent |
| | 100.0% | | (thinner) |

While only certain preferred embodiments of this invention have been shown and described by way of illustration, many modifications will occur to those skilled in the art and it is, therefore, desired that it be understood that it is intended herein, to cover all such modifications that fall within the true spirit and scope of this invention.

We claim:

1. A method of killing fungi or yeast comprising treating fungi or yeast in their habitat with toxic concentrations of dihydrocarvone.

2. The method of claim 1 for killing fungi wherein said fungi are selected from a group consisting of Microsporum, Aureobasidium, Cladosporium, and Phialophora.

3. The method of claim 1 for killing yeast wherein said yeast is Candida.